United States Patent
Phillips et al.

(10) Patent No.: US 7,020,505 B1
(45) Date of Patent: Mar. 28, 2006

(54) METHOD AND APPARATUS FOR MONITORING CEREBRAL PHYSIOLOGY

(75) Inventors: Jeffrey Owen Phillips, Ashland, MO (US); Roger Eugene Huckfeldt, Columbia, MO (US)

(73) Assignee: Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/600,012

(22) PCT Filed: Jan. 7, 1999

(86) PCT No.: PCT/IB99/00088

§ 371 (c)(1),
(2), (4) Date: Sep. 8, 2000

(87) PCT Pub. No.: WO99/34730

PCT Pub. Date: Jul. 15, 1999

(30) Foreign Application Priority Data

Jan. 8, 1998 (GB) .................................. 9800370

(51) Int. Cl.
*A61B 5/00* (2006.01)
(52) U.S. Cl. ...................... 600/310; 600/361
(58) Field of Classification Search ........ 600/309–310, 600/361, 300, 378; 604/19–21, 27–28
See application file for complete search history.

(56) References Cited

U.S. PATENT DOCUMENTS

| | | | | |
|---|---|---|---|---|
| RE31,879 E | * | 5/1985 | Lubbers et al. ............. 436/133 |
| 4,830,849 A | * | 5/1989 | Osterholm ...................... 435/4 |
| 4,903,707 A | | 2/1990 | Knute et al. |
| 4,904,237 A | * | 2/1990 | Janese .......................... 604/28 |
| 5,117,836 A | * | 6/1992 | Millar ......................... 600/561 |
| 5,403,746 A | * | 4/1995 | Bentsen et al. ............... 436/68 |
| 5,531,776 A | * | 7/1996 | Ward et al. ................... 600/16 |
| 5,579,774 A | | 12/1996 | Miller et al. |
| 5,704,352 A | * | 1/1998 | Tremblay et al. ........... 600/300 |
| 5,830,188 A | * | 11/1998 | Abouleish .................... 604/158 |
| 5,833,603 A | * | 11/1998 | Kovacs et al. .............. 600/317 |
| 5,951,476 A | * | 9/1999 | Beach ......................... 600/437 |
| 6,049,727 A | * | 4/2000 | Crothall ...................... 600/310 |

OTHER PUBLICATIONS

Enevoldsen E.M. and F.T. Jensen, "Cerebrospinal Fluid lactate and pH in patients with acute sever head injury", Clin Neurol Neurosurg, 1977; 80(4), Abstract.*

Venkatesh, B, R. Boots, F. Tomlinson, and R.D. Jones, "The continuous measurement of cerebrospinal fluid gas tensions in critically ill neurosurgical patients: a prospective observational study", Intensive Care Med, 1999; 25(6), Abstract.*

(Continued)

*Primary Examiner*—Eric F. Winakur
(74) *Attorney, Agent, or Firm*—Blackwell Sanders Peper Martin LLP

(57) ABSTRACT

A method and apparatus for predicting the outcome of head injury trauma by monitoring cerebrospinal fluid (CSF) characteristics, preferably my monitoring the pH of CSF. The apparatus includes a catheter with a wall section adapted to permit CSF to flow therein, and a sensor located within the catheter such that the CSF is permitted to flow adjacent the tip of the sensor.

29 Claims, 2 Drawing Sheets

OTHER PUBLICATIONS

Webster's New World Dictionary of American English, Webster's Now World Dictionaries, 3rd College Edition, p. 1011.*

Offbeat Outline News at http://www.info.gov.hk/police/offbeat/archives/644/news3.html (1997).*

Linda Pai, MD, Roger Huckfeldt, MD, Michael H. Metzler, MD, FACS, Jeffrey Phillips, Pharm.D., and David Jimenez, MD, FACS. Missouri Chapter American College of Surgeons, Inc., 30th Annual Professional Meeting, Jun. 13-15, 1997, "Continuous Evaluation of Cerebral Perfusion in Severe Brain Injury," p. 22.

* cited by examiner

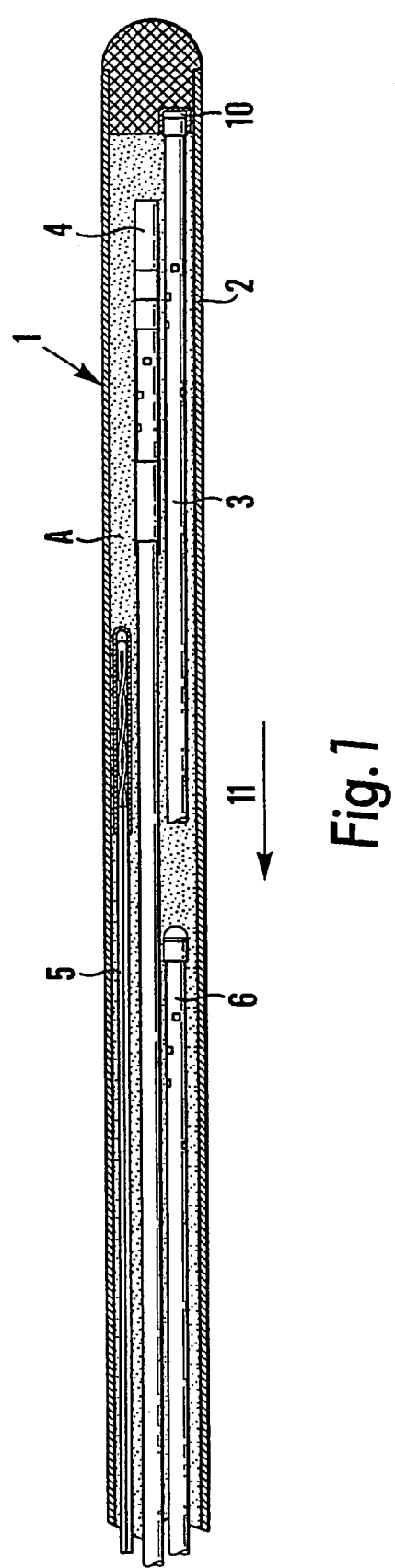
Fig.1
Fig.2

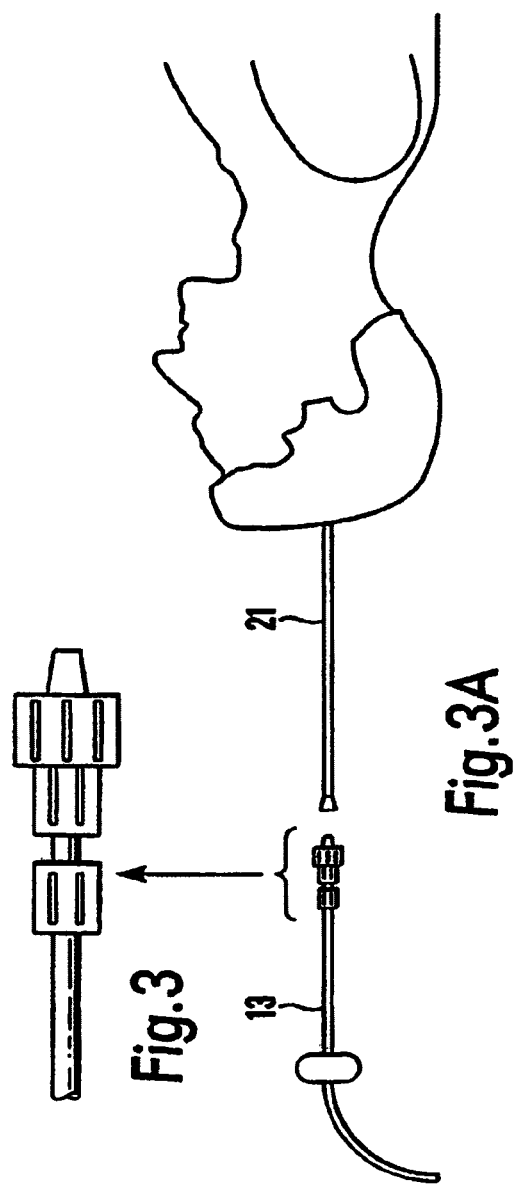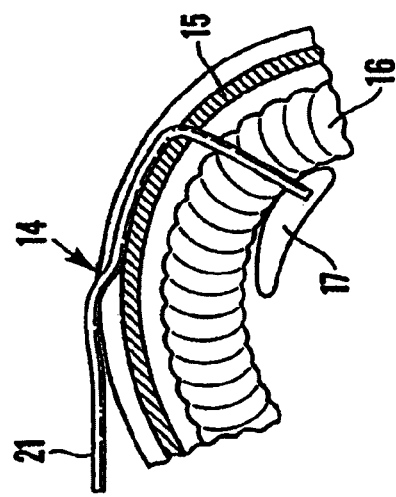
Fig. 3
Fig. 3A
Fig. 3B

METHOD AND APPARATUS FOR MONITORING CEREBRAL PHYSIOLOGY

STATEMENT REGARDING FEDERALLY SPONSORED RESEARCH OR DEVELOPMENT

Not applicable.

CROSS REFERENCE TO RELATED APPLICATIONS

Not applicable.

BACKGROUND OF THE INVENTION

This invention relates to a method and apparatus for monitoring the cerebral cellular environment, especially in patients who have sustained brain injury.

BRIEF SUMMARY OF THE INVENTION

In the event of medical incidents, such as severe trauma to the head, it is frequent practice to monitor the intracranial pressure (ICP) in a ventricle of the brain. An increase in ICP is thought to be indicative of secondary injury such as brain swelling, and it is known to be necessary to relieve pressure by draining cerebrospinal fluid (CSF) if a patient's ICP rises above a critical level. While a body of data exists in the management of intracranial hypertension there have been few investigations of the significance of other cerebral physiological parameters.

The present invention is based on this observation that the pH of CSF is an indicator of the condition of a patient's brain after suffering head trauma and thus the likely outcome of medical treatment.

According to one aspect of the present invention there is provided a method of predicting the outcome of head trauma which comprises monitoring the pH of cerebrospinal fluid (CSF) and comparing the measured pH with a base line representing brain death.

In investigations which have been carried out by the present inventors, a pH sensor was inserted into a cerebral ventricle of a patient and the pH monitored by sequential measurements. Both the rate of change of pH and the absolute level of pH were measured on a continuous basis. While a rapid decrease of pH is a strong indicator of a poor survival prognosis, the absolute value of pH can be used directly to provide a guide to the patients' well being. In general, it has been found that stable levels of pH in the region of 7.15 to 7.25 suggest that the patient is likely to improve clinically, while significantly lower pH levels or continuously falling pH levels are a pointer to poor survival chances. In one case, a pH of about 7.05 correlated with brain stem death.

The present invention also includes apparatus for monitoring the pH and optionally other cerebral physiological parameters which comprises a lumen adapted for introduction through an opening in a skull of a living patient into a cerebral ventricle, said lumen having a pH sensor therein and permitting CSF to flow thereinto and over the sensor.

Preferably, the pH sensor contains a pH-sensitive colour change or fluorescent material and the colour change or fluorescence is measured optically by determining the absorption of a standard light beam.

The catheter containing the pH probe may be a single lumen and may also be used for removing samples of CSF fluid from the ventricle. Alternatively, a bitumen catheter may be employed in which the sensor is housed in one lumen and CSF is withdrawn from the other lumen. Removal of CSF may be desirable because of a perceived increase in ICP or may be removed prior to a detected increase in ICP because of a predicted deterioration in the patients well being because of a fall in pH.

BRIEF DESCRIPTION OF THE SEVERAL VIEWS OF THE DRAWING

The invention is illustrated by reference to the accompanying drawings in which:—

FIG. 1 is a section through a tubular probe containing various sensors;

FIG. 2 is a part section through the probe;

FIG. 3 is a schematic view showing one way in which the apparatus may be connected to a patient;

FIG. 3A is an enlarged view of the Luer lock; and

FIG. 3B is a partial section through the patient's head showing one method of introducing the lumen containing the pH sensor.

DETAILED DESCRIPTION OF THE INVENTION

Referring to the drawings the apparatus comprises a tubular probe (1) comprising a microporous sheath which permits the transfer of CSF into a gel (A) filling the probe. A number of sensors are housed within the tubular probe. One of these is a pH sensor (3). Sensor 3 comprises a length of optical fibre having a mirrored distal end 10 to reflect light back towards the proximal end 11, longitudinally of the optical fibre. Several holes (12) are laser drilled through the optical fibre in a number of random directions normal to the longitudinal axis of the fibre. These holes are filled with a gel containing a phenol red dye which undergoes a colour change with change in pH. A colour change over the pH range from about 6.8 to 7.8 is desirable. The colour shade of the phenol red indicator is determined by passing a light beam along the optical fibre and measuring the absorption spectrum of the reflected beam. After calibration, the absorption spectrum of the reflected beam gives a measure of the pH of the CSF.

As indicated in FIG. 1, the tubular probe may also include other sensors such as a $CO_2$ concentration sensor ($pCO_2$), 4, a partial oxygen pressure sensor ($PO_2$), 6, and a thermocouple 5.

Tubular probe 1 is introduced into a ventriculostomy catheter 21 which has a distal end having a foraminous wall to permit CSF to flow into and around the tip of the probe.

The catheter may be introduced into the patient's skull and retained in place with a tubular skull bolt, e.g. as shown in U.S. Pat. No. 4,903,707 (the contents of which are specifically incorporated herein by reference). Conveniently, the catheter is urged into the opening in the skull as shown schematically in FIG. 3 until expression of CSF indicates that the catheter tip has reached the cerebral ventricle.

Referring to FIG. 3, the catheter 21 has a distal end into which the tip of the probe is positioned. In the Example illustrated, the catheter comprises a single lumen, e.g. of PVC or polypropylene. The catheter is connected via a Luer lock to an extension tube 13 which may incorporate a side port (not shown) for sampling CSF and monitoring ICP. The extension tube is further connected by optical fibres to a detection, monitoring and display equipment.

Apparatus which is commercially available for intravascular blood monitoring under the registered trade mark 'Paratrend' 7 (Diametrics Medical Ltd 5, Manor Court Yard, Hughendon Ave, High Wycombe, HP13 5RE, United Kingdom) may be adapted for monitoring the pH of CSF by providing means for holding the sensor lumen in place in the skull. This may involve a bolt as described in the above cited U.S. Pat. No. 4,903,707 or secured by other fixing means as indicated in FIG. 3B. Referring to this latter Figure it can be seen that the catheter 21 is fixed to the patient's head by securing means 14, passes under the scalp in contact with the skull 15 and then through an opening in the skull and brain 16 to reach a brain ventricle 17. The small, size and flexibility of the catheter (about 2–3 mm diameter) facilitates introduction of the catheter. The distal tip of the catheter is provided with holes to permit flow of CSF therethrough and around the tip of the probe which is also located within the cerebral ventricle.

EXAMPLE 16 patients admitted to hospital following brain trauma resulting in severe brain injury (GCS≦8) were included in the study. A 'Paratrend 7' sensor measuring pH, $pCO_2$ and $PO_2$ was advanced into a ventriculostomy. Sensor data was stored into a computer and transferred to a spreadsheet, pH, $pCO_2$, $PO_2$, 1CP, CPP, patent manipulation and outcome were monitored.

Six patients were excluded due to technical difficulties in obtaining and recording data early in the study.

Four patients were found to have initial pH in the range 7.15 to 7.22 but had progressive CSF acidemia over the next 24 to 48 hours. All progressed to herniation and brain death. Clinical evidence of brain death occurred as the pH approached 7.05.

Two patients were found to have a relative high initial CSF pH in the range 7.20–7.25. These values remained substantially constant and both patients remained vegetative.

In the remaining four patients initial pH was in the range 7.12 to 7.24 but increased over the following 48 hours. All displayed significant clinical recovery.

It was found that patient care activities and other known stressors were found to cause a rapid decrease in CSF pH which resolved shortly after the activity stopped. All negative changes in brain pH occurred significantly before elevations of ICP or change in CPP could be detected. This suggests that CSF pH is a more effective indicator of a patient's neurological condition since remedial action can be taken earlier. It was also noted that measurement of CSF pH provides a means for monitoring cerebral ischemia following blunt head trauma. Falling pH correlates to ongoing cellular injury and occurs well before increases in intracranial pressures.

The invention claimed is:

1. A method of monitoring the cerebral cellular environment of a patient for prognosis and for providing information for treatment comprising:
   providing an opening in the skull of said patient;
   inserting a catheter through said opening into a region of cerebrospinal fluid (CSF) within said skull of said patient, said catheter having a flow section capable of permitting said CSF to flow therein;
   positioning said flow section of said catheter into said region of CSF;
   placing at least one sensor capable of sensing pH into said flow section within said catheter to enable said CSF to flow adjacent said sensor so that said sensor may sense at least one characteristic, including pH, of said CSF;
   monitoring changes of said at least one characteristic of said CSF within the initial 48 hours following head trauma; and
   predicting the outcome of the head trauma based on the monitored changes.

2. The method of claim 1, wherein said region of CSF is a cerebral ventricle.

3. The method of claim 1, further comprising:
   fixing said catheter in place in said opening of said skull to prevent movement of said catheter relative to said opening in said skull.

4. The method of claim 1, wherein said inserting step further comprises:
   inserting said catheter into said region of CSF until expression of said CSF indicates said catheter has reached said cerebral ventricle.

5. The method of claim 1, further comprising:
   connecting said catheter to an extension tube; and
   locking said sensor within said catheter.

6. The method of claim 5, further comprising:
   draining said CSF through said catheter, wherein said monitored characteristic further includes intracranial pressure.

7. The method of claim 1, wherein said characteristic monitored further includes a characteristic selected from the group consisting of partial oxygen pressure, temperature, carbon dioxide concentration, and combinations thereof.

8. The method of claim 7, wherein the pH of said CSF is monitored and compared with a base line.

9. The method of claim 1, further comprising:
   monitoring said characteristic on a continuous basis;
   collecting data regarding said characteristic;
   storing said data; and
   comparing said data.

10. The method of claim 1, wherein said monitoring step comprises:
    monitoring said characteristic within the initial 24 hours following trauma.

11. A method of monitoring at least one characteristic of cerebrospinal fluid (CSF) of a patient for prognosis and for providing information for treatment comprising:
    providing an opening in the skull of said patient through which a region of CSF is accessible;
    inserting a catheter through said opening into said region of CSF in said patient, said catheter having a flow section capable of permitting said CSF to flow therein;
    positioning said flow section of said catheter into said region of CSF;
    placing at least one sensor capable of sensing pH into said flow section within said catheter to enable said CSF to flow adjacent said sensor so that said sensor may sense at least one characteristic, including pH, of said CSF;
    monitoring changes of said at least one characteristic of said CSF within the initial 48 hours following head trauma; and
    predicting the outcome of the head trauma based on the monitored changes.

12. The method of claim 11, further comprising;
    fixing said catheter in place in said opening of said patient to prevent movement of said catheter relative to said opening in said patient.

13. The method of claim 11, wherein said inserting step further comprises:
    inserting said catheter into said region of CSF until expression of said CSF indicates said catheter has reached said region of CSF.

14. The method of claim 11, further comprising:
connecting said catheter to an extension tube; and
locking said sensor within said catheter.

15. The method of claim 14, further comprising:
draining said CSF through said catheter.

16. The method of claim 11, wherein said characteristic monitored further includes a characteristic selected from the group consisting of partial oxygen pressures temperature, carbon dioxide concentration, and combinations thereof.

17. The method of claim 16, wherein the pH of said CSF is monitored and compared with a base line.

18. The method of claim 11, further comprising:
monitoring said characteristic on a continuous basis;
collecting data regarding said characteristic;
storing said data; and
comparing said data.

19. The method of claim 11, wherein said monitoring step comprises:
monitoring said characteristic within the initial 24 hours following trauma.

20. An apparatus for monitoring the cerebral cellular environment of a patient, comprising:
a catheter having a wall section adapted to permit cerebrospinal fluid (CSF) to flow therein, said catheter adapted for introduction through an opening in a skull of a patient; and
at least one sensor capable of sensing pH located within a porous sheath, wherein said porous sheath is located within said catheter such that said CSF is permitted to flow through said porous sheath and adjacent said sensor;
said sensor further being capable of monitoring at least one characteristic, including pH, of said CSF over time.

21. The apparatus of claim 20, wherein said catheter is a dual lumen catheter comprising a first lumen and a second lumen.

22. The apparatus of claim 21, wherein said sensor is housed in said first lumen and said CSF is drawn through said second lumen.

23. The apparatus of claim 20, wherein said characteristic monitored further includes a characteristic selected from the group consisting of partial oxygen pressure, temperature, carbon dioxide concentration, and combinations thereof.

24. The apparatus of claim 20, further comprising:
equipment for monitoring, storing, and, comparing data of said characteristic from said sensor over time.

25. An apparatus for monitoring at least one characteristic of cerebrospinal fluid (CSF) of a patient, comprising:
a catheter having a wall section adapted to permit said CSF to flow therein, said catheter adapted for introduction through an opening in said patient through which a region of CSF is accessible; and
at least one sensor capable of sensing pH located within a porous sheath, wherein said porous sheath is located within said catheter such that said CSF is permitted to flow through said porous sheath and adjacent said sensor;
said sensor further being capable of monitoring at least one characteristic, including pH, of CSF over time.

26. The apparatus of claim 25, wherein said catheter is a dual lumen catheter comprising a first lumen and a second lumen.

27. The apparatus of claim 26, wherein said sensor is housed in said first lumen and said CSF is withdrawn through said second lumen.

28. The apparatus of claim 25, wherein said characteristic monitored further includes a characteristic selected from the group consisting of partial oxygen pressure, temperature, carbon dioxide concentration, and combinations thereof.

29. The apparatus of claim 26, further comprising:
equipment for monitoring, storing, and, comparing data of said characteristic from said sensor over time.

* * * * *